United States Patent [19]
Mizukawa

[11] Patent Number: 5,214,149
[45] Date of Patent: May 25, 1993

[54] PROCESS FOR PRODUCING A 1H-PYRAZOLO[5,1-C]-1,2,4-TRIAZOLE COMPOUND

[75] Inventor: Yuki Mizukawa, Minami-ashigara, Japan

[73] Assignee: Fuji Photo Film Co., Ltd., Kanagawa, Japan

[21] Appl. No.: 644,329

[22] Filed: Jan. 22, 1991

[30] Foreign Application Priority Data

Jan. 23, 1990 [JP] Japan ................................ 2-11765

[51] Int. Cl.$^5$ ........................................... C07D 487/04
[52] U.S. Cl. .................................. 546/271; 548/262.4
[58] Field of Search ....................... 548/262.4; 546/271

[56] References Cited

U.S. PATENT DOCUMENTS 3,725,067  4/1973  Bailey et al. ..................... 548/262.4

FOREIGN PATENT DOCUMENTS 157283  7/1987  Japan .

*Primary Examiner*—Patricia L. Morris
*Attorney, Agent, or Firm*—Burns, Doane, Swecker & Mathis

[57] ABSTRACT

There are disclosed processes of producing a 1H-pyrazolo[5,1-c]-1,2,4-triazole compound by (1) the ring-formation reaction of 5-hydrazino-1H-pyrazole with a carboxylic acid and by (2) the ring-closure reaction of a 5-acylhydrazino-1H-pyrazole, wherein both the reactions are carried out in the presence of a phosfolan compound or phosphonium salt formed from a tertiary phosphine and a halogenating agent. The disclosure described provides a method of producing a 1H-pyrazolo[5,1-c]-1,2,4-triazole compound that can be carried out efficiently in one step in simplified process with improved yield compared with the prior process.

13 Claims, No Drawings

PROCESS FOR PRODUCING A 1H-PYRAZOLO[5,1-C]-1,2,4-TRIAZOLE COMPOUND

FIELD OF THE INVENTION

The present invention relates to processes for producing 1H-pyrazolo[5,1-c]-1,2,4-triazole compounds useful as couplers for silver halide color photographic materials.

BACKGROUND OF THE INVENTION 1H-pyrazolo[5,1-c]-1,2,4-triazole compounds are useful compounds as magenta couplers for silver halide color photographic materials. As processes for synthesizing these compounds, the following synthesis processes are hitherto known.

A first synthesis process is disclosed in U.S. Pat. No. 3,725,067, British Patent No. 1,252,418, or *Journal of the Chemical Society*, Parkin I (9177), pages 2047 to 2052. In this process, a 5-hydrazino-1H-pyrazole-4-carboxylate compound can be acylated to obtain a 5-acylhydrazino-1H-pyrazole-4carboxylate compound, and it is then heated together with phosphorous oxychloride for a long period of time under reflux to produce a 1H-pyrazolo[5,1-c]-1,2,4-triazole compound. However, in this process, there are two processing steps and the ring-closing step requires a higher temperature and a long reaction time. The yield of some compounds decreases and therefore improvements of the process are desired.

A second process is described in JP-A ("JP-A" means unexamined published Japanese patent application) No. 158283/1987. In this process, a 5-hydrazino-1H-pyrazole compound is acylated to obtain a 5-acylhydrazino-1H-pyrazole compound, which is reacted with thionyl chloride, followed by a ring-closure reaction in the presence of an alcohol, to produce a 1H-pyrazolo[5,1-c]-1,2,4-triazole compound. However, this process also is carried out in two steps and the reaction medium has to be replaced in the dehydration-ring-formation reaction of the 5-acylhydrazino-1H-pyrazole compound, so that the procedure is complex.

Furthermore, the above synthesis processes are both required to be carried out under strong acid conditions, and the yield of some compounds decreases extremely under these conditions.

A third synthesis process is described in JP-A No. 233285/1989. That is, either an imide acid ester or an orthoester is reacted with 5-hydrazino-1H-pyrazole to synthesize a 1H-pyrazolo[5,1-c]-1,2,4-triazole compound in one step. In this process, it is desired to improve further the yield.

As described above, the conventional processes for obtaining a 1H-pyrazolo[5,1-c]-1,2,4-triazole compound using a 5-hydrazino-1H-pyrazole as a raw material have such problems that the number of the processing steps is large, the reaction time is long, the procedure is complex, or the yield is low.

SUMMARY OF THE INVENTION

The object of the present invention is to provide processes for producing a 1H-pyrazolo[5,1-c]-1,2,4-triazole compound using as raw materials a 5-hydrazino-1H-pyrazole and, a 5-acylhydrazino-1H-pyrazole in a reduced number of steps under milder conditions in a short period of time in good yield.

Other and further objects, features, and advantages of the invention will appear more fully from the following description.

DETAILED DESCRIPTION OF THE INVENTION

The above object of the present invention has been attained by providing the processes given below.

That is, the present invention provides (1) a process for producing a 1H-pyrazolo[5,1-c]-1,2,4-triazole compound wherein the ring-formation reaction of a 5-hydrazino-1H-pyrazole between a carboxylic acid is carried out in the presence of a phosfolan or a phosphonium salt formed from a tertiary phosphine and a halogenating agent, and (2) a process for producing a 1H-pyrazolo[5,1-c]-1,2,4-triazole compound wherein the ring-closure reaction of a 5-acylhydrazino-1H-pyrazole is carried out in the presence of a phosfolan compound or a phosphonium salt formed from a tertiary phosphine and a halogenating agent.

The above present processes are processes for producing a 1H-pyrazolo[5,1-c]-1,2,4-triazole compound represented by the following formula (II), characterized in that a tertiary phosphine represented by the following formula (I) is used in the dehydration condensation step.

$(Y)_3P$            (I)

wherein Y represents an alkyl group, an aryl group, an alkoxy group, an aryloxy group, or an amino group.

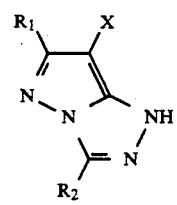

Formula (II)

wherein $R_1$ represents a hydrogen atom or a substituent, $R_2$ represents a hydrogen atom, an alkyl group, an aryl group, or a heterocyclic group, and X represents a hydrogen atom or a substituent.

More particularly, in the present invention, a 1H-pyrazolo[5,1-c]-1,2,4-triazole compound represented by the above-mentioned formula (II) is produced by dehydrating and condensing reaction between a 5-hydrazino-1H-pyrazole represented by the following formula (III) and a carboxylic acid represented by the following formula (IV) by using a phosfolan compound represented by the following formula (VII) or a phosphonium salt represented by the following formula (VI) formed from a tertiary phosphine represented by the above-mentioned formula (I) and a halogenating agent represented by the following formula (V)

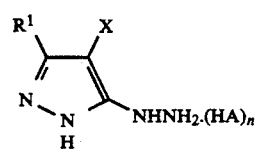

Formula (III)

wherein $R_1$ and X have the same meanings as defined above, A represents an acid radical, and n is 0 or a positive number required to neutralize the charge in the molecule

  (IV)

wherein $R_2$ has the same meaning as defined above and M represents a hydrogen atom or an alkali metal

  (V)

wherein Hal represents a halogen atom and Q represents a substituent $[(Y)_3P—Hal]^+Q^-$  (VI)

wherein Y, Hal, and Q have respectively the same meanings as defined above and

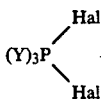  Formula (VII)

wherein Y and Hal have respectively the same meanings as defined above.

Further, in the present invention, a 1H-pyrazolo[5,1-c]-1,2,4-triazole compound represented by the above-mentioned formula (II) is produced by causing a phosfolan compound represented by the above-mentioned formula (VII) or a phosphonium salt represented by the above-mentioned formula (VI) formed from a tertiary phosphine represented by the above-mentioned formula (I) and a halogenating agent represented by the above-mentioned formula (V) to interact with a 5-acylhydrazino-1H-pyrazole represented by the following formula (VIII)

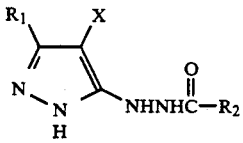  Formula (VIII)

wherein $R_1$, $R_2$, and X have respectively the same meanings as defined above.

It is considered that the reaction in the process of the present invention would proceed as shown in the following scheme:

Scheme (1)

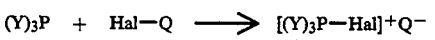
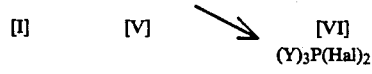
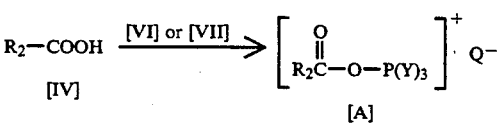

-continued
Scheme (1)

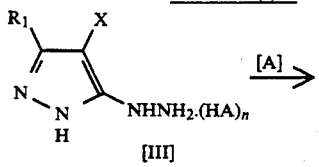
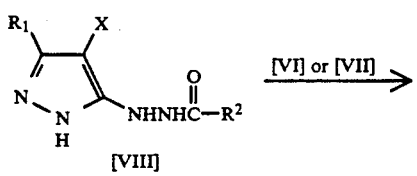
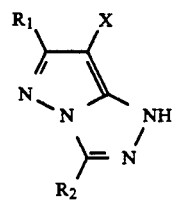

$R_1$ of the 5-hydrazino-1H-pyrazole represented by formula (III) used as a starting raw material represents a hydrogen atom or a substituent. The substituent can be, for example, an alkyl group, an aryl group, a heterocyclic group, an alkoxy group, an aryloxyl group, a heterocyclic oxy group, an alkylthio group, an arylthio group, a heterocyclic thio group, an amino group, an anilino group, an acylamino group, a ureido group, a urethane group, an alkoxycarbonyl group, a sulfonamido group, a sulfamoyl group, a sulfonyl group, a cyano group, a nitro group, or a hydroxyl group. The substituent will be described in more detail. The alkyl group denotes a straight-chain or branched, substituted or unsubstituted alkyl group having 1 to 50 carbon atoms. The substituent of the substituted alkyl group denotes a halogen atom (e.g., fluorine, chlorine, and bromine), a cyano group, a nitro group, an aryl group (e.g., phenyl and naphthyl), a heterocyclic group (e.g., 1-pyrazolyl and 1-imidazolyl), an alkoxy group (e.g., methoxy, ethoxy, isopropyloxy, butoxy, and dodecyloxy), an aryloxy group (e.g., phenoxy, 2,4-di-t-amylphenoxy, and 3-methanesulfonamidophenoxy), an alkylthio group (e.g., methylthio, ethylthio, butylthio, octylthio, and hexadecylthio), an arylthio group (e.g., phenylthio and naphthylthio), an amino group (e.g., dimethylamino, diethylamino, diphenylamino, and diisopropylamino), an acylamino group (e.g., N-methylacetylamino and N-butyltetradecanoylamino), a ureido group (N,N,N'-triethylureido), a urethane group (e.g., N-butyl-phenylurethane and N-octylethylurethane), an alkoxycarbonyl group (e.g., methoxycarbonyl, ethoxycarbonyl, and dodecyloxycarbonyl), a sulfonamido group (e.g., methanesulfonamido, ethanesulfonamido, hexadecanesulfonamido, and p-toluenesulfonamido), a sulfamoyl group (e.g., N-methylsulfamoyl, N-butylsulfamoyl, N,N-diethylsulfamoyl, and N,N-dioctylsulfamoyl), or a sulfonyl group (e.g., methylsulfonyl, ethylsulfonyl, butylsulfonyl, octylsulfonyl, hexadecylsulfonyl, and phenylsulfonyl). Two or more of such substituents may be present. If there are two or more substituents, they may be the same or different. The aryl group denotes a substituted or unsubstituted aryl group, and the substituent of the substituted aryl group has the same meaning as that of the substituent described for the above substituted alkyl group. A heterocyclic group, an alkoxy group, an aryloxy group, a heterocyclic oxy group, and an alkylthio group represented by $R_1$ may have the substituent described for the above substituted alkyl group (e.g., methoxy, ethoxy, propyloxy, butyloxy, isopropyloxy, t-butoxy, 2-phenoxyethoxy, 2-methanesulfonylethoxy, and 2-(2,4-di-t-amylphenoxyethoxy), an aryloxy group (e.g., phenoxy, 2-methoxyphenoxy, 2,4-dimethoxyphenoxy, 2,6-dimethoxyphenoxy, 2,4-di-t-amylphenoxy, and 2-ethoxycarbonyphenoxy), a heterocyclic oxy group, an alkylthio group (e.g., methylthio, ethylthio, butylthio, and hexadecylthio), an arylthio group (e.g., phenylthio, naphthylthio, 2-ethoxycarbonylphenylthio, and 2-butoxy-5-t-octylphenylthio), a heterocyclic thio group, an amino group (e.g., dimethylamino, diisopropylamino, and dibutylamino), an anilino group (e.g., 2,5-dichloroanilino and 2-ethoxycarbonylanilino), an acylamino group (e.g., N-methylacetylamino, N-phenylacetylamino, and N-butylpivaloylamino), a ureido group (e.g., N,N,N'-triethylureido), a urethane group (e.g., N-methylphenylurethane), an alkoxycarbonyl group (e.g., methoxycarbonyl, ethoxycarbonyl, and dodecyloxycarbonyl), a sulfonamido group (e.g., methanesulfonamido, ethanesulfonamido, hexadecanesulfonamido, N-methyloctanesulfonamido, and p-toluenesulfonamido), a sulfamoyl group (e.g., N-butylsulfamoyl, methylsulfamoyl, ethylsulfamoyl, and phenylsulfamoyl), a cyano group, a nitro group, and a hydroxyl group.

The group represented by X is a hydrogen atom or a substituent. The substitutent is a halogen atom or a monovalent group having at least two atoms selected from a group consisting of C, N, O, S, P, and H. Preferably, X represents, for example, a hydrogen atom, a halogen atom, a cyano group, a nitro group, an alkoxycarbonyl group, a 3- to 10-membered heterocyclic group containing O, N, or S as a hetero atom, an aryloxy group, an alkoxy group, a heterocyclic oxy group, an alkylthio group, or an arylthio group.

More particularly, X represents a hydrogen atom, a halogen atom (e.g., fluorine, chlorine, and bromine), a cyano group, a nitro group, an alkoxycarbonyl group (e.g., methoxycarbonyl and ethoxycarbonyl), a heterocyclic group (e.g. pyrazolyl and imidazolyl), an aryloxy group (e.g., phenoxy, 4-methylphenoxy, 4-cyanophenoxy, 2-ethoxycarbonylphenoxy, and 4-methoxycarbonylphenoxy), an alkoxy group (e.g., methoxy and ethoxy), a heterocyclic oxy group, an alkylthio group (e.g., methylthio, dodecylthio, and 1-ethoxycarbonyldodecylthio), or an arylthio group (e.g., phenylthio, 2-pivaloylamidophenylthio, and 2-butoxy-5-t-octylphenylthio).

A represents an inorganic or organic radical. As the inorganic radical, for example, a hydrochloride radical and a sulfate radical can be mentioned, and as the organic radical, for example, a methanesulfonate radical and a para-toluenesulfonate radical can be mentioned. n represents a positive number required to neutralize the charge in the molecule, preferably 0 or 1.

Typical specific examples of the compound represented by formula (III) are shown below, but the present invention is not restricted by them.

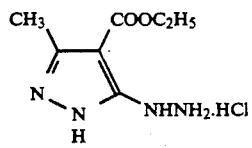

III-1

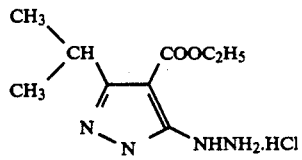

III-2

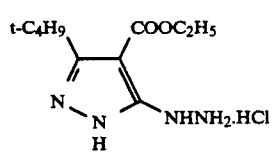

III-3

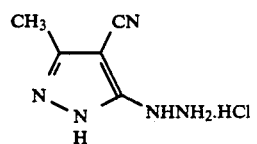

III-4

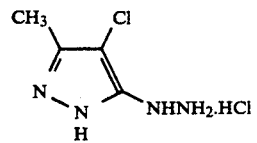

III-5

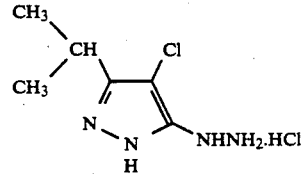

III-6

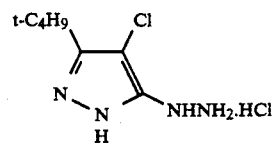

III-7

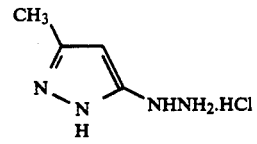

III-8

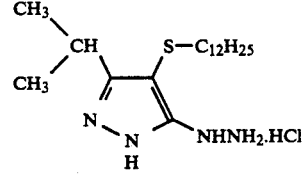

III-9

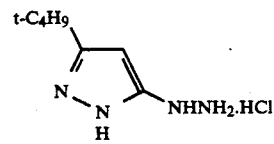

III-10

-continued
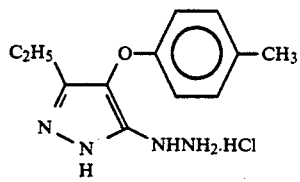
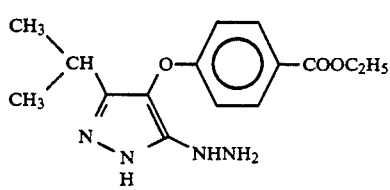
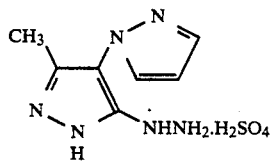
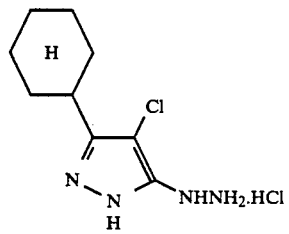
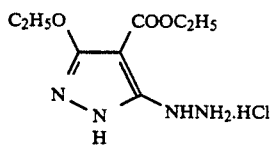
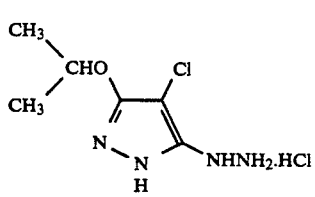
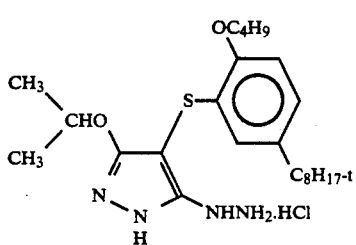
-continued
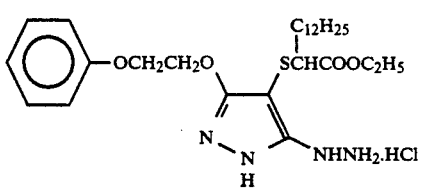
III-11
III-12
III-13
III-14
III-15
III-16
III-17
III-18
III-19
III-20
III-21
III-22
III-23
III-24
III-25
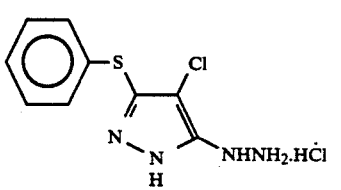

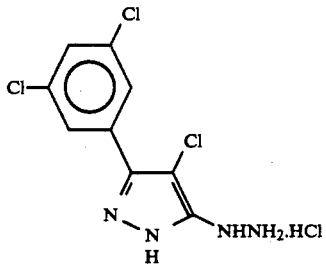
III-26

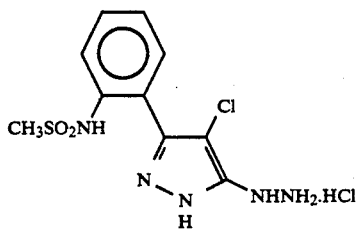
III-27

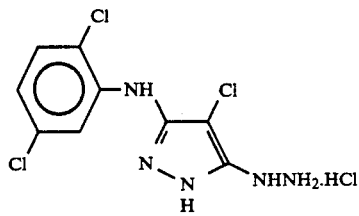
III-28

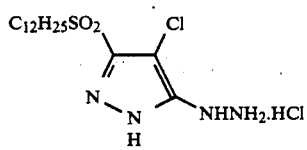
III-29

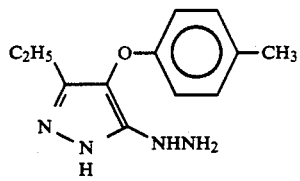
III-30

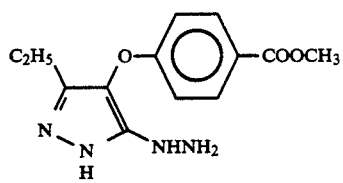
III-31

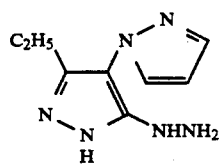
III-32

The starting raw material used in the present invention, i.e., the 5-hydrazino-1H-pyrazole compound represented by formula (III), is obtained by diazotizing the corresponding 5-amino-1H-pyrazole compound in a usual manner followed by reduction. For example, it can be synthesized by the process described in *Organic Synthesis Collective Volume*, Vol. I, page 22, or in *Journal of the Chemical Society*, 1971, page 167.

$R_2$ of the carboxylic acid represented by formula (IV) represents a hydrogen atom, an alkyl group, an aryl group, or a heterocyclic group. $R_2$ is described in more detail below. The alkyl group denotes, for example, a straight-chain or branched, substituted or unsubstituted alkyl group having 1 to 50 carbon atoms, and the substituent of the substituted alkyl group includes a halogen atom (e.g., fluorine, chlorine, and bromine), an alkoxy group (e.g., methoxy, ethoxy, butoxy, 2-ethylhexyloxy, and hexadecyloxy), an aryloxy group (e.g., phenoxy, p-nitrophenoxy, o-chlorophenoxy, and 2,4-di-t-amylphenoxy), an aryl group (e.g., phenyl and naphthyl), an alkylthio group (e.g., methylthio, ethylthio, octylthio, and hexadecylthio), an arylthio group (e.g., phenylthio, p-dodecyloxyphenylthio, and 2-butoxy-5-t-octylphenylthio), an amino group (e.g., dimethlamino, diethylamino, and diisopropylamino), an alkoxycarbonyl group (e.g., methoxycarbonyl, ethoxycarbonyl, butoxycarbonyl, and dodecyloxycarbonyl), an aryloxycarbonyl group (e.g., phenoxycarbonyl and p-nitrophenoxycarbonyl), a sulfonamido group (e.g., methanesulfonamido, butanesulfonamido, p-toluenesulfonamido, and p-ethoxycarbonylbenzenesulfonamido), a sulfonyl group (e.g., methylsulfonyl, ethylsulfonyl, hexadecylsulfonyl, and phenylsulfonyl), a cyano group, or a nitro group. Two or more of these substituents may be present, and they may be the same or different. The aryl group denotes a substituted aryl group or an unsubstituted aryl group (e.g., phenyl and naphthyl) and the substituent of the substituted aryl group has the same meaning as that of the above-mentioned alkyl group. The heterocyclic group represented by $R_2$ denotes a substituted or unsubstituted heterocyclic group (preferably 5- to 7-membered heterocyclic group having at least one of N, S, and O as a hetero atom), and the substituent of the substituted heterocyclic group has the same meaning as that of the substituent described for the above substituted alkyl group. As the heterocyclic can be mentioned, for example, 3-pyridyl, 4-pyridyl, and 5-nitro-3-pyridyl.

Preferably $R_2$ is an alkyl group or aryl group that is substituted at 1-position by a hetero atom (e.g., aryloxy group and arylsulfonamido group), because the yield of the present invention becomes effectively high in that case.

M represents a hydrogen atom or an alkali metal (e.g., Na, K, and Ca).

Typical specific examples of the carboxylic acid represented by formula (IV) are given below, but the prevent invention is not restricted by them.

| | |
|---|---|
| CH₃COOH | IV-1 |
| C₄H₉COOH | IV-2 |
| t-C₄H₉COOH | IV-3 |
| 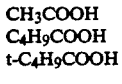 C₄H₉CHCOOH | IV-4 |
| C₁₃H₂₇COOH | IV-5 |
| C₆H₁₃OCH₂CH₂COOH | IV-6 |
| 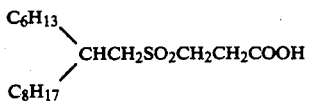 | IV-7 |

-continued
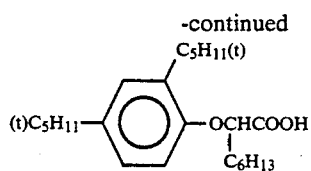 IV-8
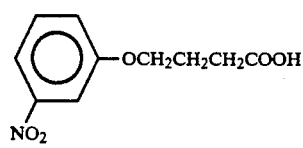 IV-9
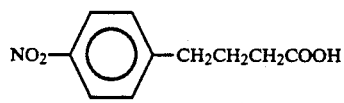 IV-10
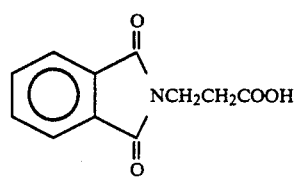 IV-11
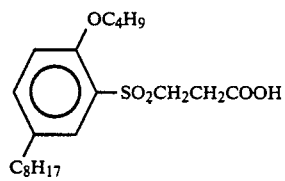 IV-12
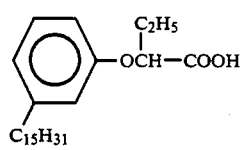 IV-13
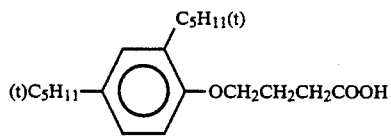 IV-14
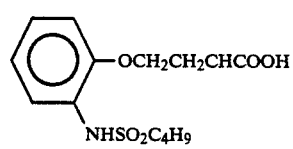 IV-15
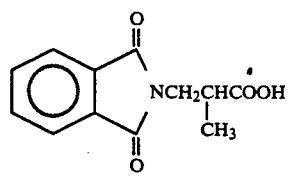 IV-16
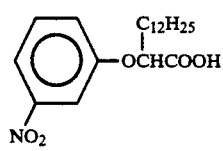 IV-17
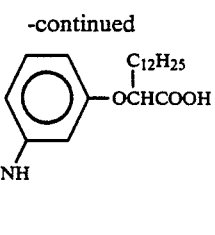 IV-18
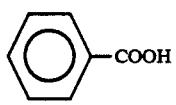 IV-19
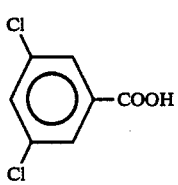 IV-20
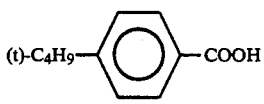 IV-21
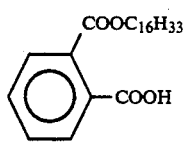 IV-22
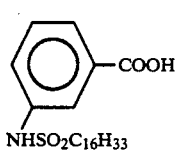 IV-23
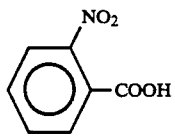 IV-24
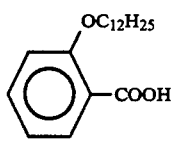 IV-25
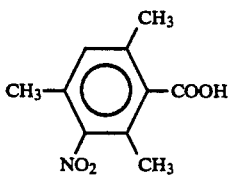 IV-26
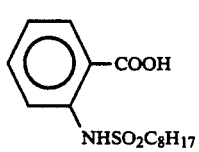 IV-27

-continued

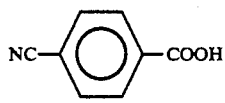  IV-28

NCCH₂COOH  IV-29

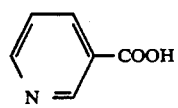  IV-30

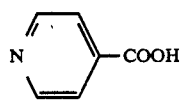  IV-31

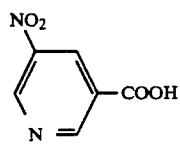  IV-32

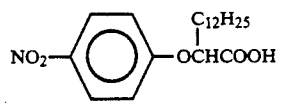  IV-33

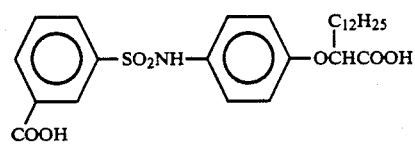  IV-34

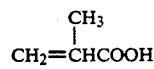  IV-35

CH₂=CHCOOH

η-C₇H₁₅COOH  IV-36

IV-37

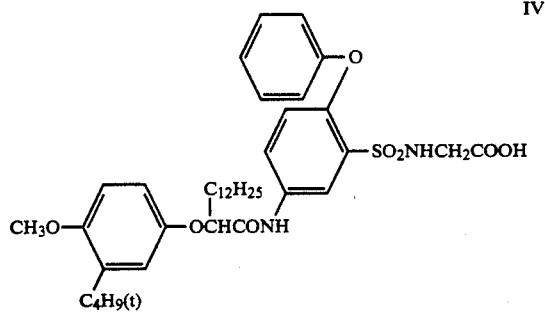

IV-38

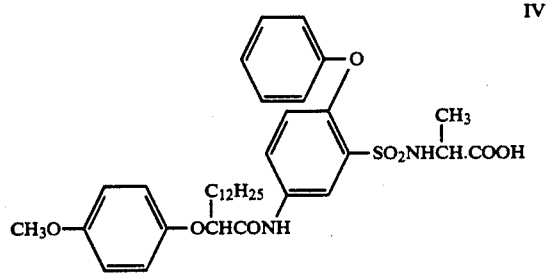

Y of the tertiary phosphine represented by formula (I) denotes an alkyl group, an aryl group, an alkoxy group, an aryloxy group, or an amino group, and more particularly the alkyl group denotes a straight-chain or branched, substituted or unsubstituted alkyl group hav-ing 1 to 10 carbon atoms. The substituent of the substituted alkyl group has the same meaning as that of the substituted alkyl group represented by $R_1$ of the amidoxime compound represented by formula (III), and two or more of such substituents may be present. The two or more substituents may be the same or different. The aryl group denotes a substituted or unsubstituted aryl group, and the substituent of the substituted aryl group has the same meaning as that of the above-mentioned substituted alkyl group. Examples of the alkoxy group are methoxy, ethoxy, propyloxy, butyloxy, and isopropyloxy; examples of the aryloxy group are phenoxy and naphthyloxy, and examples of the amino group are dimethylamino, diethylamino, dipropylamino, dibutylamino, and diisopropylamino. Preferably Y denotes an aryl group or an amino group, with a phenyl group being particularly preferred.

$\left( \phenyl \right)_3 P$  I-1

$\left( \begin{array}{c} CH_3 \\ CH_3 \end{array} N \right)_3 P$  I-2

$(CH_3)_3 P$  I-3

$(C_2H_5)_3 P$  I-4

$(CH_3O)_3 P$  (I-5)

$(C_2H_5O)_3 P$  I-6

$(C_4H_9O)_3 P$  I-7

$\left( \begin{array}{c} C_2H_5 \\ C_2H_5 \end{array} N \right)_3 P$  I-8

$(C_4H_9)_3 P$  I-9

Hal of halogenating agent represented by formula (V) represents a halogen atom (e.g., chlorine and bromine), Q represents a substituent. The substituent represents a halogen atom (e.g., chlorine and bromine), an imido group (e.g., succinimide and phthalimide), a halogenated alkyl group (e.g., trichloromethyl, tribromomethyl, pentachloroethyl, and pentabromoethyl).

Preferable examples of halogenating agent represented by formula (V) are shown below, but the invention is not limited to them.

| | |
|---|---|
| Cl₂ | V-1 |
| Br₂ | V-2 |
| CCl₄ | V-3 |
| CBr₄ | V-4 |

-continued

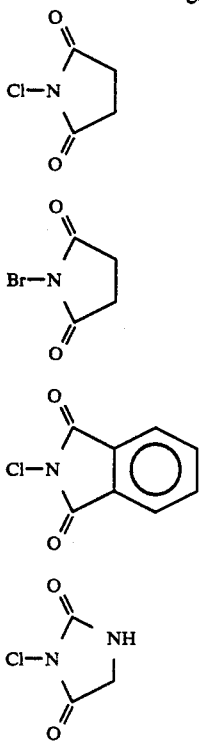

Y, Hal, and Q of the phosphonium salt represented by formula (VI) and the phosfolan compound represented by formula (VI) have respectively the same meanings as those described for formulae (I) and (V).

$R_1$, X, and $R_2$ of the 5-acylhydrazino-1H-pyrazole represented by formula (VIII) have respectively the same meanings as those described for formulae (III) and (IV). The 5-acylhydrazino-1H-pyrazole can be synthesized easily by using the present dehydration condensation agent, and it can also be synthesized from the 5-hydrazino-1H-pyrazole represented by formula (III) and the acid halide represented by formula (IV).

Typical specific examples of the 5-acylhydrazino-1H-pyrazole represented by formula (VIII) can be obtained by combining arbitrarily a 5-hydrazino-1H-pyrazole represented by formula (III) and a carboxylic acid represented by formula (IV), but the present invention is not restricted by them.

The 1H-pyrazolo[5,1-c]-1,2,4-triazole compound obtained by the present process is represented by the following formula (II):

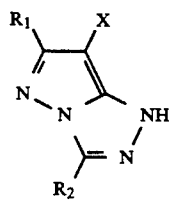

Formula (II)

wherein $R_1$, X, and $R_2$ have respectively the same meanings as those described for the above-mentioned formulae (III) and (IV).

Typical specific examples of the compound represented by formula (II) are given below, but the present invention is not restricted by them.

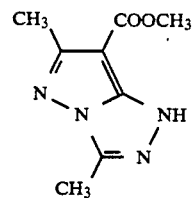 II-1

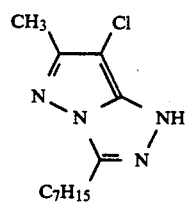 II-2

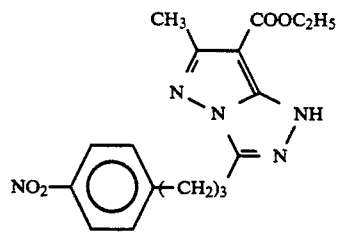 II-3

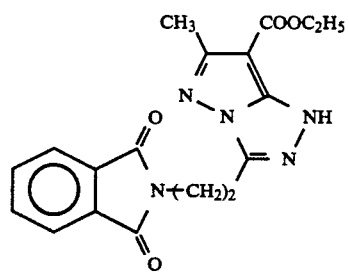 II-4

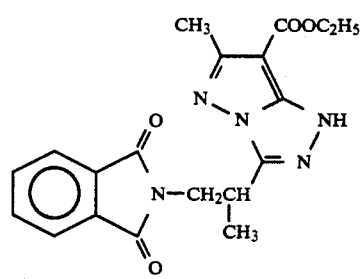 II-5

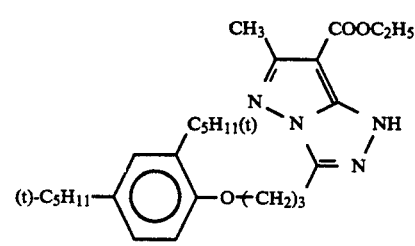 II-6

-continued
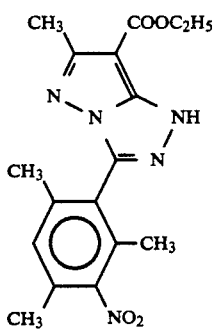  II-7
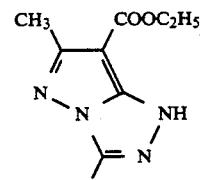  II-8
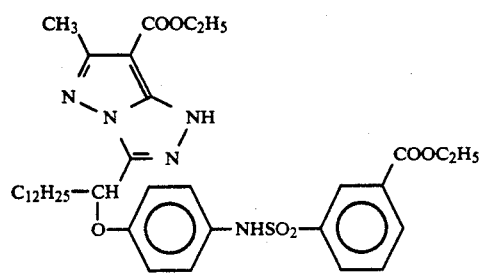  II-9
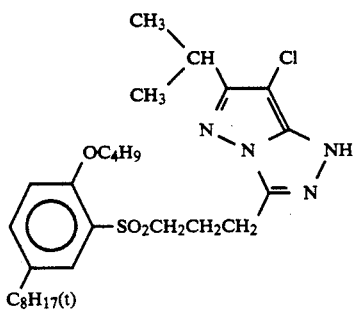  II-10
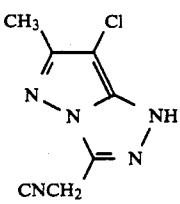  II-11
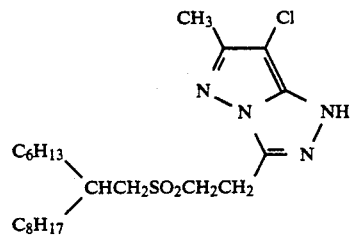  II-12
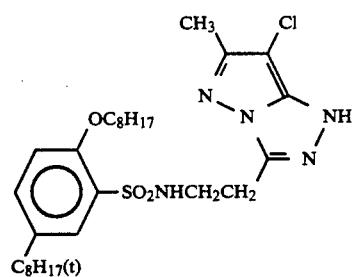  II-13
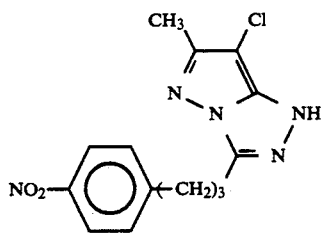  II-14
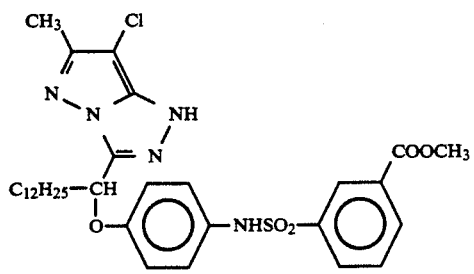  II-15
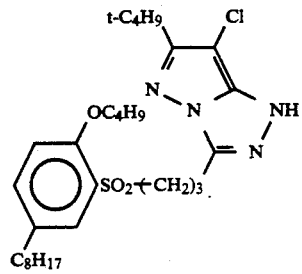  II-16

-continued
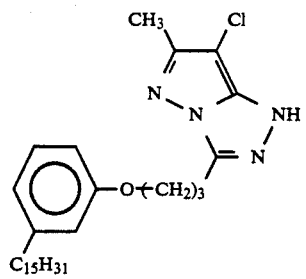 II-17
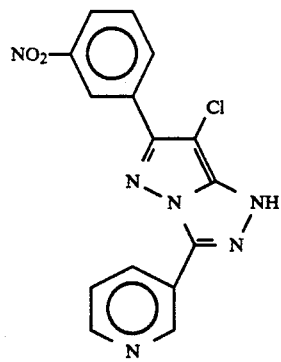 II-18
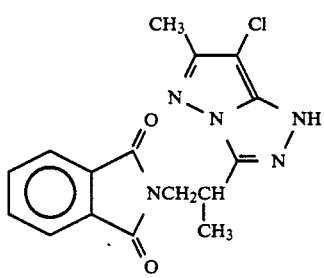 II-19
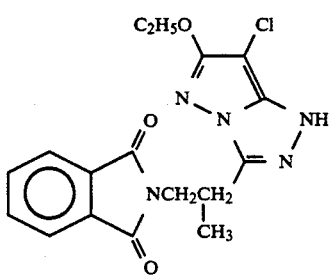 II-20
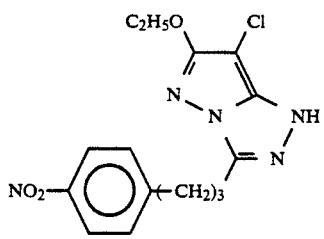 II-21
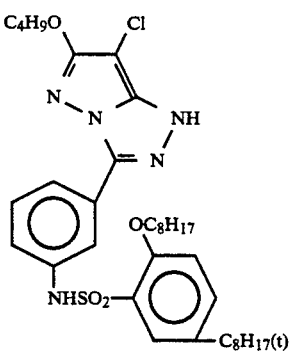 II-22
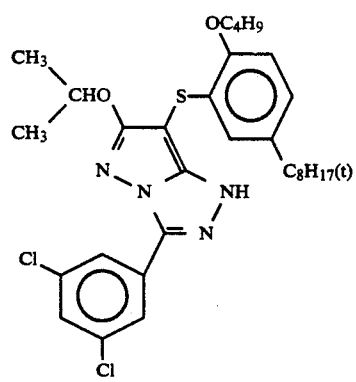 II-23
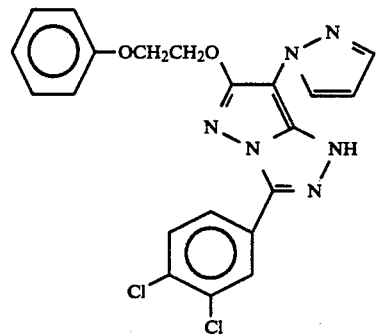 II-24

-continued
II-25 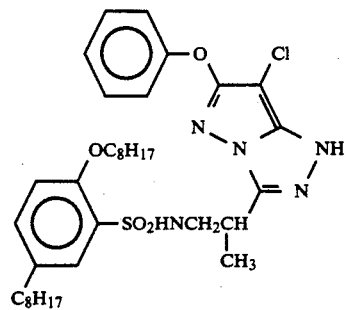
II-26 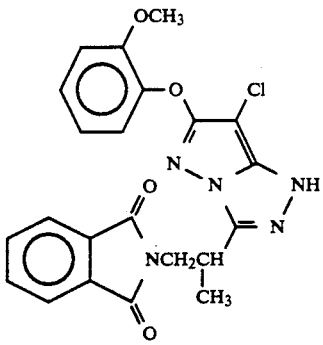
II-27 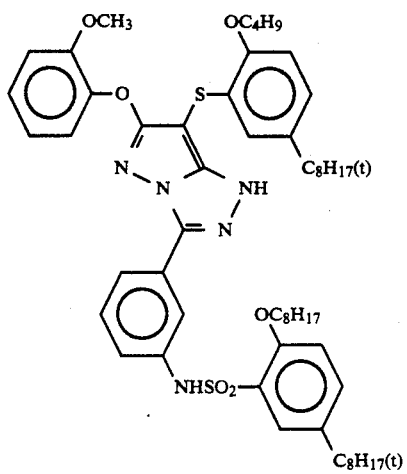
II-28 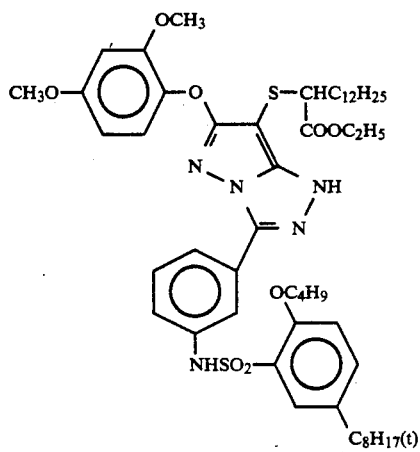
II-29 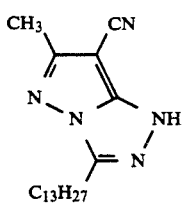
II-30 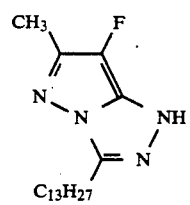
II-31 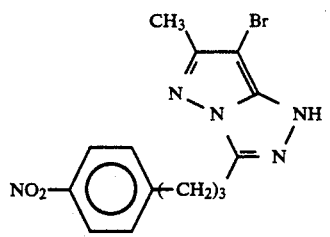
II-32 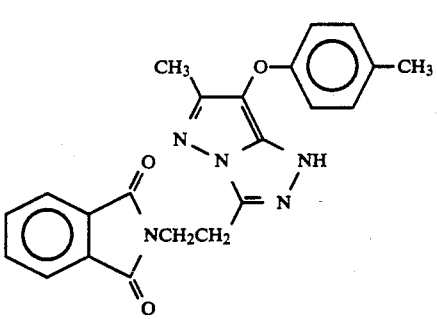
II-33 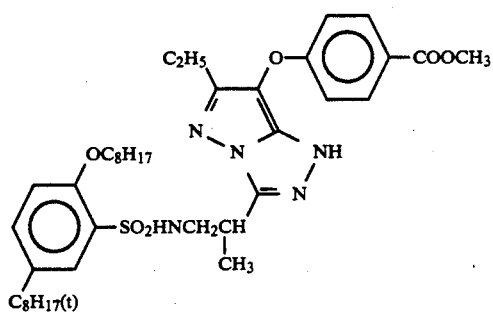
II-34 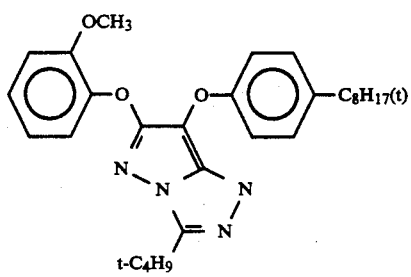

II-35
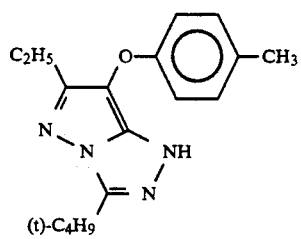
II-36
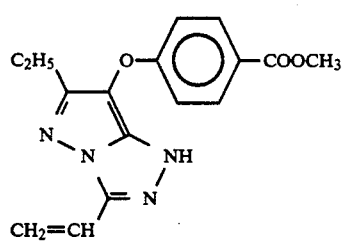
II-37
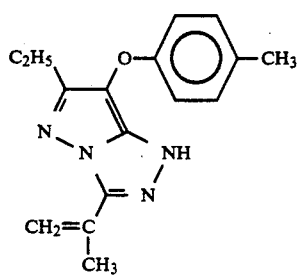
II-38
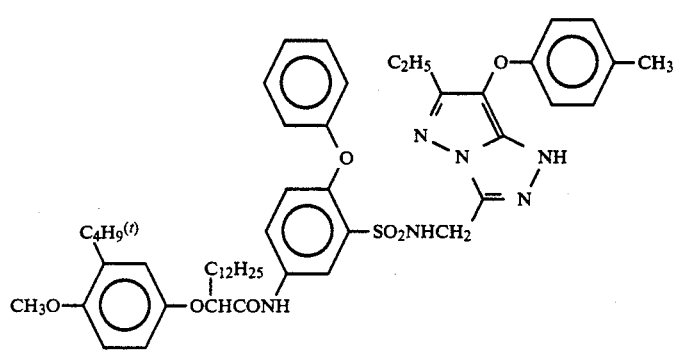
II-39
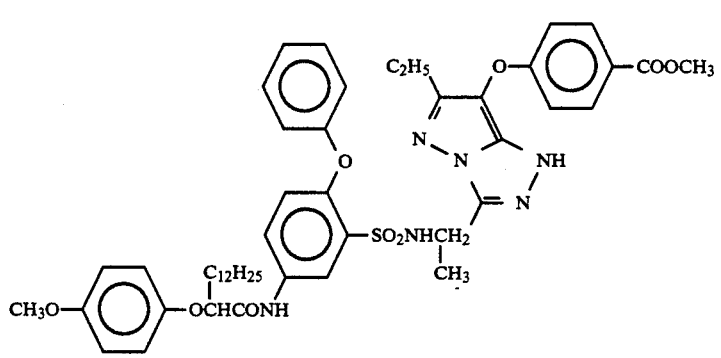
II-40
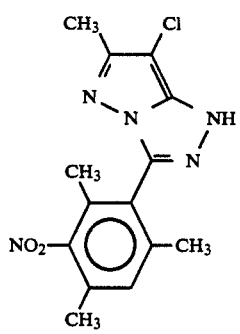
II-41
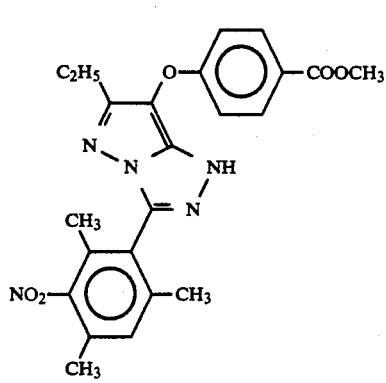

II-42

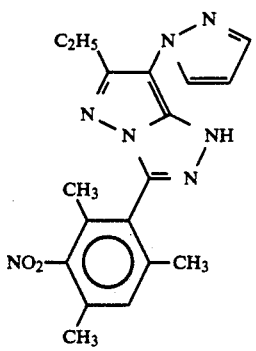

In the present invention the dehydration condensation reaction between a 5-hydrazino-1H-pyrazole represented by formula (III) and a carboxylic acid represented by formula (IV) that uses a tertiary phosphine represented by formula (I) and a halogegating agent represented by formula (V) may be carried out without any solvent, or it may be carried out by dissolving or dispersing them in a suitable solvent. As typical solvents usable in the present invention, acetonitrile, dimethylsulfoxide, sulfolane, dimethylacetamide, dimethylimidazolidone, tetrahydrofuran, ethyl acetate, 1,2-dimethoxyethanebenzene, and toluene can be mentioned. Polar solvents, such as acetonitrile, are preferable. These solvents may be used alone or as a mixture of two or more of them.

The amount of the solvent to be used is 1 to 1000 pts. wt., preferably 1 to 30 pts. wt., for one pts. wt. of the compound represented by formula (III).

To prepare a compound represented by formula (VIII) or (II), a compound represented by formula (III) and a carboxylic acid represented by formula (IV) are used in a molar ratio of 1:1 to 1:20. Preferably, the molar ratio is 1:1 to 1:20 if the reaction is carried out without any solvent, and preferably the molar ratio is 1:1 to 1:3 if the reaction is carried out using the solvent as mentioned above.

Although the compound represented by formula (III) can be used in the reaction in the form of a salt of an acid, as shown in Scheme (1), it can be used in the reaction in the free form by previously adding an organic base, such as trialkylamines (e.g., trimethylamine and triethylamine), dialkylanilines (e.g., N,N-diethylaniline), pyridines (e.g., 2,4,6-trimethylpyridine, pyridine, and dimethylaminopyridine), quinolines (e.g., quinoline), DBU, or DABCO, to the reaction system, or it can be used in the reaction by adding an inorganic base, such as sodium carbonate, potassium carbonate, potassium hydrogencarbonate, or sodium silicate, or above-mentioned organic base, after the reaction between the compound represented by formula (VIII) and the compound represented by formula (VI) or (VII) has proceeded sufficiently. In the present invention, an organic base is used preferably. The molar amount of the base to be used is 1 to 20, preferably 1 to;5, times the amount of compound represented by formula (III).

The compound represented by formula (III) and the compound represented by formula (I) are used in a molar ratio of 1:1 to 1:10, more preferably 1:2 to 1:10.

The compound represented by formula (VIII) and the compound represented by formula (I) are used in a molar ratio of 1:1 to 1:10, more preferably 1:1 to 1:5.

The compound represented by formula (I) and the compound represented by formula (V) are used in a molar ratio of 1:1 to.1:100, preferably 1:1 to 1:5.

The reaction temperature may be −10° to 150° C., preferably −10° to 100° C., and particularly preferably -10° to 80° C.

The reaction will be completed in 30 min to 20 hours when the reaction temperature is −10° to 150° C.

Although the above has described the case wherein the reaction is started from a compound represented by formula (III), if a compound represented by formula (VIII) is subjected to dehydration and condensation, the reaction conditions, including the solvent, the type of phosphines, the reaction temperature, and the reaction time, are substantially the same.

According to the present manufacturing process, a desired 1H-pyrazolo-[5,1-c]-1,2,4-triazole compound can be produced efficiently in one step from a 5-hydrazino-1H-pyrazole and a carboxylic acid and the process can be simplified. Further the low yield of a compound that was obtained starting from a 5-acylhydrazino-1H-pyrazole by the prior manufacturing process can be improved considerably. Furthermore, according to the present process, an excellent effect that a 1H-pyrazolo-[5,1-c]-1,2,4-triazole compound can be produced in a short period of time under mild conditions, not under strong acid or high temperature conditions, can be exhibited.

Now, specific Examples of the present invention will be described, but the present invention is not restricted by them.

EXAMPLE 1

Example 1: Exemplified Compound II-3

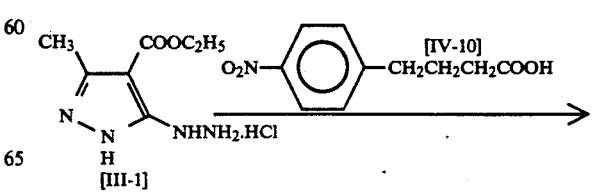

-continued

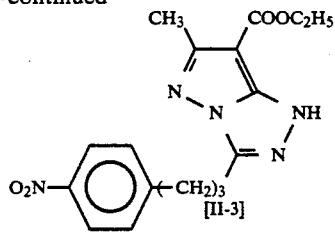

350 ml of acetonitrile was added to 22.0 g (0.1 mol) of 5-hydrazino-1H-pyrazole [III-1], and the mixture was cooled to 5° to 10° C. with stirring. 20.2 g (0.2 mol) of triethylamine was added dropwise thereto, and then 20.9 g (0.1 mol) of 4-(p-nitrophenyl)butane acid [VI-10] and 78.7 g (0.3 mol) of triphenylphosphine were added. 40.0 g (0.3 mol) of N-chlorosuccinimide was added to the solution in portions with stirring at 0° to 5° C. After the completion of the addition, stirring was continued for 2 hours at 0° to 5° C. and then for 5 hours at room temperature. After the completion of the reaction, when water was added to the reaction liquid, a gum deposited. The gum was washed with water, then the water was removed, acetonitrile was added, and when they were stirred at room temperature, crystals deposited. The crystals were filtered and dried, to obtain 22.7 g (63.5 %) of the exemplified compound II-3. The melting point was 122° to 128° C.

Example 2: Exemplified Compound II-15 dropwise. After a further 12 g of triphenylphosphine was added, they were stirred for 2 hours. After the completion of the reaction, the reaction mixture was poured in to water and extraction with ethyl acetate was carried out. The ethyl acetate layer was washed with water and the ethyl acetate was distilled off under reduced pressure. The residue was refined by silica gel column chromatography (the eluting solution: n-hexane/ethyl acetate) and then recrystallized from acetonitrile, to obtain 37.2 g (48.1%) of the exemplified compound II-15. The melting point was 128° to 129° C. The results are shown in Table 1.

EXAMPLES 3 AND 4

Experiment was carried out in the same manner as in Example 1, except that, as a pyrazole, Compound III-5, and as a carboxylic acid, Compound IV-36 were used, thereby synthesizing the exemplified compound II-2. The results are shown as Example 3 in Table 1. Example I was repeated, except that, as a carboxylic acid, Compound IV-14 was used, thereby synthesizing the exemplified compound II-6. The results are shown as Example 4 in Table 1.

EXAMPLES 5, 6, 7, 8, 9 10, 11, AND 12

Experiment were carried out in the same manner as in Example 2, except that the compound of formula (VIII) was changed, thereby preparing the corresponding exemplified compounds II-3, II-10, and II-12. Further, experiment were carried out in the same manner as in Example 2, except that the compound of formula (VIII)

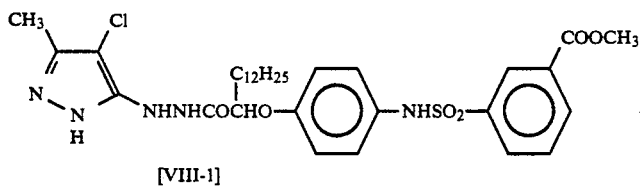

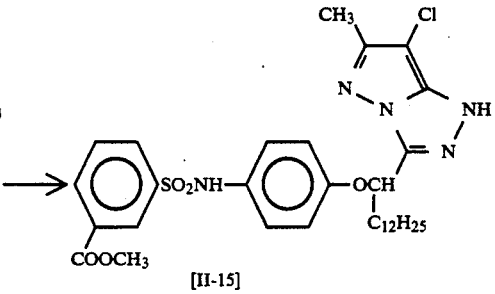

800 ml of acetonitrile was added to 79.5 g of acylhydrazine [VIII-1] and 46 ml of carbon tetrachloride and they were cooled with ice to 0° C. and stirred. 47.2 g of triphenylphosphine was added to the solution, and after they were stirred at 10° C. or below for 3 hours, a further 12 g of triphenylphosphine was added thereto. Then, 16 μm of 2,4,6-trimethylpyridine was added was changed and trimethylpyridine was changed to triethylamine in an equimolar amount, thereby preparing the corresponding exemplified compound II-38, II-39, II-40, II-41, and II-42. The results are shown as Examples 5, 6, 7, 8, 9, 10, 11 and 12 in Table 1.

TABLE 1

| Example No. | Exemplified Compound No. | $R_1$ | $R_2$ | X | Yield (%) | mp (°C.) |
|---|---|---|---|---|---|---|
| Example 1 | II-3 | CH$_3$— | —(CH$_2$)$_3$—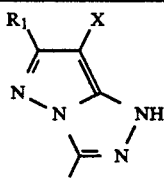—NO$_2$ | —COOC$_2$H$_5$ | 73.5 | 122~128 |

TABLE 1-continued

[Structure: pyrazole-triazole fused ring with $R_1$, $X$, and $NH$ substituents]

| Example No. | Exemplified Compound No. | $R_1$ | $R_2$ | X | Yield (%) | mp (°C.) |
|---|---|---|---|---|---|---|
| Example 2 | II-15 | " | $-CHO \langle C_{12}H_{25} \rangle -\!\!\bigcirc\!\!-NHSO_2-\!\!\bigcirc\!\!-COOCH_3$ | —Cl | 48.1 | 128~129 |
| Example 3 | II-2 | " | $-C_7H_{15}(n)$ | " | 55.1 | 92~93 |
| Example 4 | II-6 | " | $+CH_2)_3-\!\!\bigcirc\!\!\langle C_5H_{11}(t), C_5H_{11}(t) \rangle$ | $-COOC_2H_5$ | 68.6 | Oily product |
| Example 5 | II-3 | " | $+CH_2)_3-\!\!\bigcirc\!\!-NO_2$ | " | 92.0 | 122~128 |
| Example 6 | II-10 | $(CH_3)_2CH-$ | $+CH_2)_3SO_2-\!\!\bigcirc\!\!\langle OC_4H_9, C_8H_{17}(t) \rangle$ | —Cl | 65.3 | 120~122 |
| Example 7 | II-12 | $CH_3-$ | $-CH_2CH_2SO_2CH_2CH\langle C_6H_{13}, C_8H_{17} \rangle$ | —Cl | 70.2 | 55~60 |
| Example 8 | II-38 | $C_2H_5-$ | $-CH_2NHSO_2-\!\!\bigcirc\!\!(O\!\!-\!\!\bigcirc)-NHCOCHO\!\!-\!\!\bigcirc\!\!\langle C_4H_9(t), OCH_3 \rangle$ with $C_{12}H_{25}$ | $-O-\!\!\bigcirc\!\!-OCH_3$ | 83 | 162~163 |
| Example 9 | II-39 | $C_2H_5-$ | $-CHNHSO_2-\!\!\bigcirc\!\!(O\!\!-\!\!\bigcirc)-NHCOCHO\!\!-\!\!\bigcirc\!\!-OCH_3$ with $CH_3$ and $C_{12}H_{25}$ | $-O-\!\!\bigcirc\!\!-COOCH_3$ | 68 | Glassy state |
| Example 10 | II-40 | $CH_3-$ | mesityl with $CH_3, CH_3, CH_3, NO_2$ | —Cl | 93.8 | 225~227 |
| Example 11 | II-41 | $C_2H_5-$ | mesityl with $CH_3, CH_3, CH_3, NO_2$ | $-O-\!\!\bigcirc\!\!-COOCH_3$ | 70.3 | 270~275 (Decomposed) |
| Example 12 | II-42 | The same as the above | The same as the above | $-N\!\!\langle\text{pyrazolyl}\rangle$ | 85.6 | 249~250 |

Comparative Example: Synthesis of exemplified compound II-15

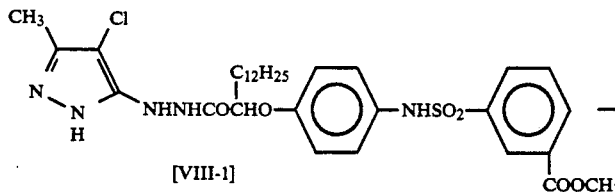
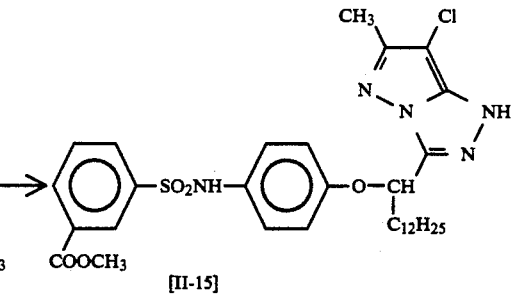

Synthesis is carried out according to the synthesis process described in U.S. Pat. No. 3,725,067. That is, 3.31 g of Compound (VIII-1) was added to 10 ml of toluene and they were heated and stirred. 1.8 ml of phosphorus oxychloride was added dropwise thereto. After the completion of the addition., the mixture was heated for 20 hours with stirring. The reaction liquid was poured in to ice-water and extraction with ethyl acetate was carried out. The ethyl acetate solution was washed with water, followed by drying, and the ethyl acetate was distilled off under reduced pressure. The residue was refined by column chromatography and recrystallized from acetonitrile, thereby obtaining 0.3 g (4.2% of the theoretical yield) of the exemplified compound II-15. The melting point was 128° to 129° C., which was the same as that of Example 2.

Synthesis was carried out according to the synthesis process described in JP-A No. 158283/1987, and the yield was as low as the above.

Having described our invention as related to the embodiment, it is our intention that the invention be not limited by any of the details of the description, unless otherwise specified, but rather be construed broadly within its spirit and scope as set out in the accompanying claims.

What we claim is:

1. A method of producing a 1H-pyrazolo[5,1-c]-1,2,4-triazole compound which comprises causing a ring-formation reaction between a 5-hydrazino-1H-pyrazole compound represented by formula (III)

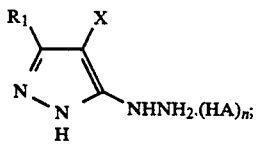  (III)

wherein $R_1$ represents a hydrogen atom, an alkyl group, a phenyl group, an alkoxy group, a phenyloxy group, an alkylthio group, a phenylthio group, an amino group, an anilino group, an acylamino group, a ureido group, a urethane group, an alkoxycarbonyl group, a sulfonamido group, a sulfamoyl group, a sulfonyl group, a cyano group, a nitro group, or a hydroxyl group, and wherein the groups of $R_1$ may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, X represents a hydrogen atom, a halogen atom, a cyano group, a nitro group, an alkoxycarbonyl group, a pyrazolyl group, an imidazolyl group, a phenyloxy group, an alkoxy group, an alkylthio group, or a phenylthio group, A represents a hydrochloride radical, a sulfate radical, a methanesulfonate radical and a para-toluenesulfonate radical, and n is 0, or 1;

and a carboxylic acid represented by formula (IV):

$$R_2-COOM \qquad (IV)$$

wherein $R_2$ represents a hydrogen atom, an alkyl group, a phenyl group, a naphthyl group or a heterocyclic group selected from 3-pyridyl, 4-pyridyl, and 5-nitro-3-pyridyl, and wherein $R_2$ may have one or more substituents each substituent selected from the group of a halogen atom, an alkoxy group, a phenyloxy group, a phenyl group, an alkylthio group, a phenylthio group, an amino group, an alkoxycarbonyl group, a phenyloxycarbonyl group, a sulfonamido group, a sulfonyl group, a cyano group,

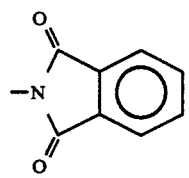

or a nitro group, and M represents a hydrogen atom or an alkali metal;

in the presence of a phosfolan compound or a phosphonium salt wherein the phosfolan compound is represented by the following formula (VII) and the phosphonium salt is represented by the following formula (VI):

$$((Y)_3P-Hal)^+Q \qquad (VI);$$

wherein Y represents an alkyl group, a phenyl group, an alkoxy group, a phenyloxy group, or an amino group, and wherein the groups of Y may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, Hal represents a halogen atom, and Q represents a halogen atom, an imido group or a halogenated alkyl group:

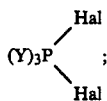 (VII)

wherein Y and Hal have the same meanings as defined above, said phosfolan compound or said phosphonium salt being formed from a tertiary phosphine and a halogenating agent represented by formula (V):

 (V);

wherein Hal and Q have the same meanings as defined above;
to form the 1H-pyrazolo[5,1-c]-1,2,4-triazole compound which is represented by formula (II):

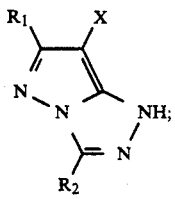 (II)

wherein $R_1$, $R_2$ and X have the same meanings as defined above.

2. A method of producing a 1H-pyrazolo[5,1-c]-1,2,4-triazole compound which comprises causing a ring-closure reaction of a 5-acylhydrazino-1H-pyrazole compound represented by the following formula (VIII):

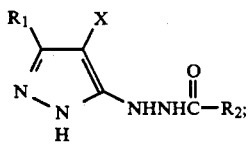 (VIII)

wherein $R_1$ represents a hydrogen atom, an alkyl group, a phenyl group, an alkoxy group, a phenyloxy group, an alkylthio group, a phenylthio group, an amino group, an anilino group, an acylamino group, a ureido group, a urethane group, an alkoxycarbonyl group, a sulfonamido group, a sulfamoyl group, a sulfonyl group, a cyano group, a nitro group, or a hydroxyl group, and wherein the groups of $R_1$ may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, X represents a hydrogen atom, a halogen atom, a cyano group, a nitro group, an alkoxycarbonyl group, a pyrazolyl group, an imidazolyl group, a phenyloxy group, an alkoxy group, an alkylthio group, or a phenylthio group, and $R_2$ represents a hydrogen atom, an alkyl group, a phenyl group, a naphthyl group or a heterocyclic group selected from 3-pyridyl, 4-pyridyl, and 5-nitro-3-pyridyl, wherein the alkyl group, phenyl group, naphthyl group or heterocyclic group of $R_2$ may have one or more substituents each substituent selected from the group of a halogen atom, an alkoxy group, a phenyloxy group, a phenyl group, an alkylthio group, a phenylthio group, an amino group, an alkoxycarbonyl group, a phenyloxycarbonyl group, a sulfonamido group, a sulfonyl group, a cyano group,

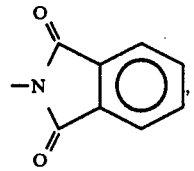

in the presence of a phosfolan compound or phosphonium salt wherein the phosfolan compound is represented by the following formula (VII) and the phosphonium salt is represented by the following formula (VI):

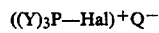 (VI);

wherein Y represents an alkyl group, a phenyl group, an alkoxy group, a phenyloxy group, or an amino group, an wherein the groups of Y may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, Hal represents a halogen atom, and Q represents a halogen atom, an imido group or a halogenated alkyl group:

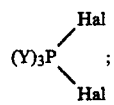 (VII)

wherein Y and Hal have the same meanings as defined above, said phosfolan compound or said phosphonium salt being formed from a tertiary phosphine and a halogenating agent represented by formula (V):

 (V);

wherein Hal and Q have the same meanings as defined above;
to form the 1H-pyrzolo[5,1-c]-1,2,4-triazole compound which is represented by formula (II):

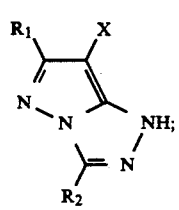 (II)

wherein $R_1$, $R_2$ and X have the same meanings as defined above.

3. A method of producing a 1H-pyrazolo[5,1-c]-1,2,4-triazole compound which comprises causing a ring-formation reaction between a 5-hydrazino-1H-pyrazole compound represented by formula (III):

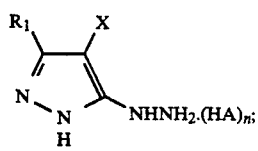

wherein $R_1$ represents a hydrogen atom, an alkyl group, a phenyl group, an alkoxy group, a phenyloxy group, an alkylthio group, a phenylthio group, an amino group, an anilino group, an acylamino group, a ureido group, a urethane group, an alkoxycarbonyl group, a sulfonamido group, a sulfamoyl group, a sulfonyl group, a cyano group, a nitro group, or a hydroxyl group, and wherein the groups of $R_1$ may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, X represents a hydrogen atom, a halogen atom, a cyano group, a nitro group, an alkoxycarbonyl group, a pyrazolyl group, an imidazolyl group, a phenyloxy group, an alkoxy group, an alkylthio group, or a phenylthio group, A represents a hydrochloride radical, a sulfate radical, a methanesulfonate radical and a para-toluenesulfonate radical, and n is 0 or 1;

and a carboxylic acid represented by formula (IV):

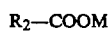

wherein $R_2$ is selected from:

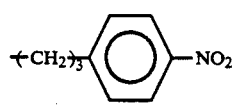

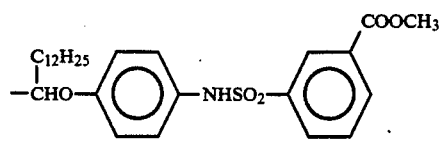

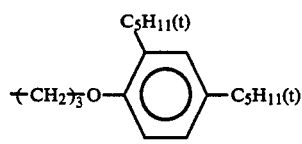

-continued

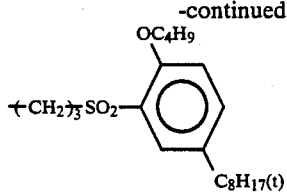

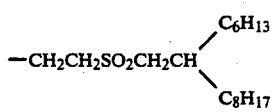

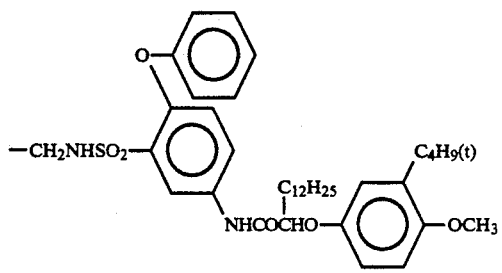

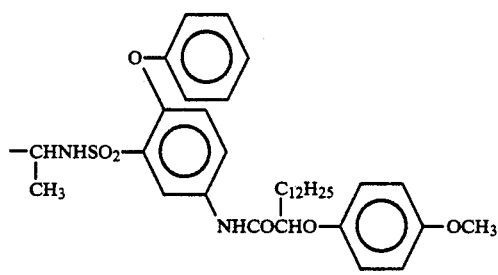

or

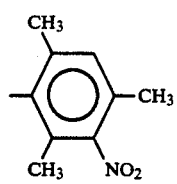

in the presence of a phosfolan compound or a phosphonium salt wherein the phosfolan compound is represented by the following formula (VII) and the phosphonium salt is represented by the following formula (VI):

wherein Y represents an alkyl group, a phenyl group, an alkoxy group, a phenyloxy group, or an amino group, and wherein the groups of Y may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, Hal represents a halogen atom, and Q represents a halogen atom, an imido group or a halogenated alkyl group:

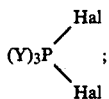

wherein Y and Hal have the same meanings as defined above, said phosfolan compound or said phosphonium salt being formed from a tertiary phosphine and a halogenating agent represented by formula (V):

wherein Hal and Q have the same meanings as defined above;
to form the 1H-pyrazolo[5,1-c]-1,2,4-triazole compound which is represented by formula (II):

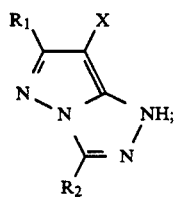

wherein $R_1$, $R_2$ and X have the same meanings as defined above.

4. A method of producing a 1H-pyrazolo[5,1-c[-1,2,4-triazole compound which comprises causing a ring-closure reaction of a 5-acylhydrazino-1H-pyrazole compound represented by the following formula (VIII):

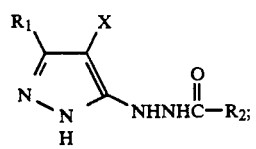

wherein $R_1$ represents a hydrogen atom, an alkyl group, a phenyl group, an alkoxy group, a phenyloxy group, an alkylthio group, a phenylthio group, an amino group, an anilino group, an acylamino group, a ureido group, a urethane group, an alkoxycarbonyl group, a sulfonamido group, a sulfamoyl group, a sulfonyl group, a cyano group, a nitro group, or a hydroxyl group, and wherein the groups of $R_1$ may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, X represents a hydrogen atom, a halogen atom, a cyano group, a nitro group, an alkoxycarbonyl group, a pyrazolyl group, an imidazolyl group, a phenyloxy group, an alkoxy group, an alkylthio group, or a phenylthio group, and $R_2$ is selected from:

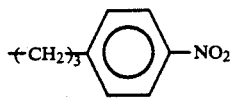

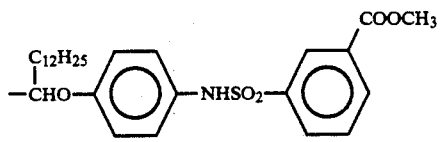

—$C_7H_{15}(n)$

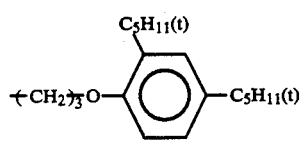

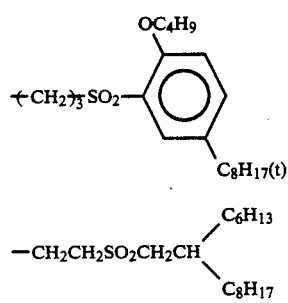

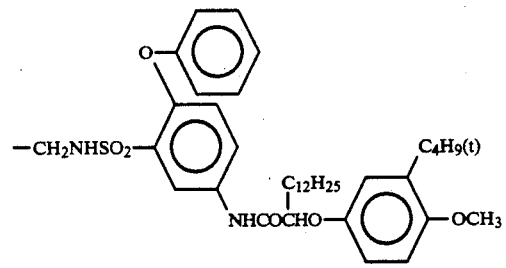

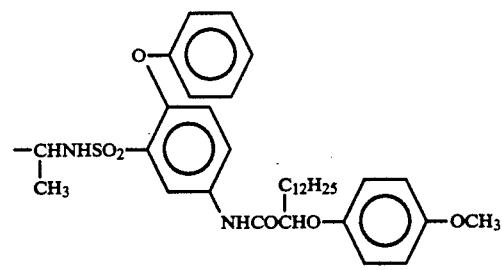

or

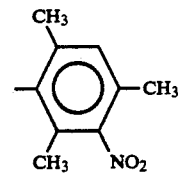

in the presence of a phosfolan compound or phosphonium salt wherein the phosfolan compound is represented by the following formula (VII) and the phosphonium salt is represented by the following formula (VI):

$((Y)_3P-Hal)^+Q^-$ (VI);

wherein Y represents an alkyl group, a phenyl group, an alkoxy group, a phenyloxy group, or an amino group, and wherein the groups of Y may have one or more substituents each substituent selected from the group of a halogen atom, a cyano group, a nitro group, a phenyl group, a naphthyl group, 1-pyrazolyl group, 1-imidazolyl group, an alkoxy group, a phenyloxy group, an alkylthio group, a phenylthio group, a naphthylthio group, an amino group, an acylamino group, a ureido group, a urethane group, an alkoxycarbonyl group, a sulfonamido group, a sulfamoyl group, or a sulfonyl group, Hal represents a halogen atom, and Q represents a halogen atom, an imido group or a halogenated alkyl group:

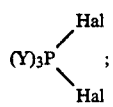 (VII)

wherein Y and Hal have the same meanings as defined above, said phosfolan compound or said phosphonium salt being formed from a tertiary phosphine and a halogenating agent represented by formula (V):

Hal—Q (V);

wherein Hal and Q have the same meanings as defined above;
to form the 1H-pyrazolo[5,1-c]-1,2,4-triazole compound which is represented by formula (II):

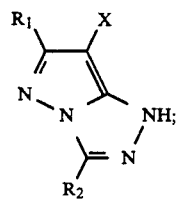 (II)

wherein $R_1$, $R_2$ and X have the same meanings as defined above.

5. The method of claim 1 wherein Q is selected from chlorine, bromine, succinimide, phthalimide, trichloromethyl, tribromomethyl, pentachloroethyl, and pentabromoethyl.

6. The method of claim 1 wherein the compound represented by formula (III) and the carboxylic acid represented by formula (IV) are reacted in a molar ratio of 1:1 to 1:20.

7. The method of claim 1 wherein the compound represented by formula (III) and the compound represented by formula (VI) or (VII) are present in a molar ratio of 1:1 to 1:10.

8. The method of claim 1 wherein the reaction between the 5-hydrazino-1H-pyrazole and the carboxylic acid is carried out for 30 minutes to 20 hours at −10° C. to 150° C.

9. The method of claim 1 wherein X is selected from

—COOC$_2$H$_5$

—Cl

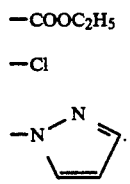

10. The method of claim 2 wherein Q is selected from chlorine, bromine, succinimide, phthalimide, trichloromethyl, tribromomethyl, pentachloroethyl, and pentabromoethyl.

11. The method of claim 2 wherein the reaction is carried out for 30 minutes to 20 hours at −10° C. to 150° C.

12. The method of claim 2 wherein X is selected from

—COOC$_2$H$_5$

—Cl

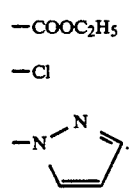

13. The method of claim 2 wherein the 5-acylhydrazino-1H-pyrazole compound and the compound represented by formula (VI) or (VII) are present in a molar ratio of 1:1 to 1:10.

* * * * *

UNITED STATES PATENT AND TRADEMARK OFFICE
CERTIFICATE OF CORRECTION

PATENT NO. : 5,214,149
DATED : May 25, 1993
INVENTOR(S) : Mizukawa

It is certified that error appears in the above-identified patent and that said Letters Patent is hereby corrected as shown below:

Column 34, line 12, after the formula insert --or a nitro group;--.

Column 34, line 57, delete "1H-pyrzolo" and insert therefor --1H-pyrazolo--.

Column 36, line 66, after "halogen atom," insert --and M represents a hydrogen atom or an alkali metal,--.

Column 36, line 45, insert --and M represents a hydrogen atom or an alkali metal--.

Signed and Sealed this

Third Day of June, 1997

Attest:

BRUCE LEHMAN

*Attesting Officer*    Commissioner of Patents and Trademarks